(12) United States Patent
Isse

(10) Patent No.: US 12,383,017 B2
(45) Date of Patent: *Aug. 12, 2025

(54) BIOCOMPOSITE MATERIAL AND METHOD FOR FORMING A BIOCOMPOSITE MATERIAL

(71) Applicant: NIKE, Inc., Beaverton, OR (US)

(72) Inventor: Jose Isse, Beaverton, OR (US)

(73) Assignee: NIKE, Inc., Beaverton, OR (US)

( * ) Notice: Subject to any disclaimer, the term of this patent is extended or adjusted under 35 U.S.C. 154(b) by 869 days.

This patent is subject to a terminal disclaimer.

(21) Appl. No.: 16/740,840

(22) Filed: Jan. 13, 2020

(65) Prior Publication Data

US 2020/0221811 A1    Jul. 16, 2020

Related U.S. Application Data

(60) Provisional application No. 62/792,784, filed on Jan. 15, 2019.

(51) Int. Cl.
*A43B 1/00* (2006.01)
*B29D 35/14* (2010.01)
(Continued)

(52) U.S. Cl.
CPC .............. *A43B 1/00* (2013.01); *B29D 35/142* (2013.01); *B33Y 80/00* (2014.12); *D06M 16/00* (2013.01);
(Continued)

(58) Field of Classification Search
CPC ........... A43B 1/00; A43B 1/0063; A43B 1/02; A43B 1/04; A43B 13/00; A43B 13/04;
(Continued)

(56) References Cited

U.S. PATENT DOCUMENTS 9,555,395 B2    1/2017   Araldi et al.
11,277,979 B2 *  3/2022   Greetham ............... A01G 18/20
(Continued)

FOREIGN PATENT DOCUMENTS

EP    3114951 A1    1/2017
EP    3239373 A1   11/2017
(Continued)

OTHER PUBLICATIONS

Jiang, L., "Manufacturing of mycelium-based biocomposites," Proceedings of the 2013 Society of the Advancement of Material and Process Engineering (SAMPE), Jun. 6, 2013, Long Beach, California, 16 pages.
(Continued)

*Primary Examiner* — Lynda Salvatore
(74) *Attorney, Agent, or Firm* — Shook, Hardy & Bacon L.L.P.

(57) ABSTRACT

A biocomposite material and methods and systems for forming a biocomposite material are provided. In one example, a biocomposite material includes a biopolymer material and an internal structure imparting zonal properties to the biocomposite material, where the biopolymer material at least partially surrounds and/or extends through the internal structure. The biopolymer material includes mycelium grown from a fungal strain.

15 Claims, 8 Drawing Sheets

(51) Int. Cl.
| | |
|---|---|
| *B33Y 80/00* | (2015.01) |
| *D06M 16/00* | (2006.01) |
| *D06N 3/00* | (2006.01) |

(52) U.S. Cl.
CPC .... *D06N 3/0086* (2013.01); *B29K 2995/0056* (2013.01)

(58) Field of Classification Search
CPC .............. A43B 23/021; A43B 23/0215; A43D 2200/60; B29D 35/12; B29D 35/122; B29D 35/126; B29D 35/142; B29K 2995/0056; B33Y 70/10; B33Y 80/00; C12P 1/02; D06M 16/00; D06N 3/00; D06N 3/0086

See application file for complete search history.

(56) References Cited

U.S. PATENT DOCUMENTS

| | | | |
|---|---|---|---|
| 2014/0310985 A1 | 10/2014 | Tran et al. | |
| 2015/0033620 A1* | 2/2015 | Greetham | A01G 18/40 800/295 |
| 2015/0223552 A1* | 8/2015 | Love | A43C 15/02 12/142 P |
| 2018/0014468 A1 | 1/2018 | Ross et al. | |
| 2018/0146627 A1 | 5/2018 | Ross et al. | |
| 2018/0282529 A1* | 10/2018 | Kaplan-Bie | D06N 3/00 |
| 2020/0221812 A1* | 7/2020 | Isse | A43B 23/0265 |
| 2022/0088292 A1 | 3/2022 | Warner et al. | |

FOREIGN PATENT DOCUMENTS

| | | |
|---|---|---|
| WO | 2016168563 A1 | 10/2016 |
| WO | 2020/018963 | 1/2020 |

OTHER PUBLICATIONS

Jiang, L. et al. "A New Process for Manufacturing Biocomposite Laminate and Sandwich Parts using Mycelium as a Binder," Proceedings of the American Society for Composites—29th Technical Conference (ACS 2014); 16th US-Japan Conference on Composite Materials; ASTM-D30 Meeting, Sep. 8, 2014, San Diego, California, 18 pages.

Haneef, M. et al., "Advanced Materials From Fungal Mycelium: Fabrication and Tuning of Physical Properties," Scientific Reports, vol. 7, No. 41292, Jan. 24, 2017, 12 pages.

Jiang, L. et al., "Manufacturing of biocomposite sandwich structures using mycelium-bound cores and preforms," Journal of Manufacturing Processes, vol. 28, No. 1, Aug. 2017, 10 pages.

Silverman, J., "Development and Testing of Mycelium-Based Composite Materials for Shoe Sole Applications," Masters Thesis, University of Delaware, Department of Fashion and Apparel Studies, Available as Early as Jan. 2018, 84 pages.

Camere, S. et al., "Fabricating materials from living organisms: An emerging design practice," Journal of Cleaner Production, vol. 186, Jun. 10, 2018, 16 pages.

Jiang, L. et al., "Bioresin infused then cured mycelium-based sandwich-structure biocomposites: Resin transfer molding (RTM) process, flexural properties, and simulation," Journal of Cleaner Production, vol. 207, Jan. 10, 2019, 14 pages.

Attias, N. et al., "Mycelium bio-composites in industrial design and architecture: Comparative review and experimental analysis," Journal of Cleaner Production, vol. 246, Feb. 10, 2020, 18 pages.

Silverman, J. et al., "Development of Mushroom Mycelium Composites for Footwear Products," Clothing and Textiles Research Journal, vol. 38, No. 2, Apr. 2020, 16 pages.

ISA European Patent Office, International Search Report and Written Opinion Issued in Application No. PCT/US2020/013388, Apr. 24, 2020, WIPO, 17 pages.

Isse, J., "Wearable Article and Method for Forming a Wearable Article," U.S. Appl. No. 16/741,080, filed Jan. 13, 2020, 48 pages.

International Preliminary Report on Patentability received for PCT Patent Application No. PCT/US2020/013309, mailed on Jul. 29, 2021, 11 pages.

International Preliminary Report on Patentability received for PCT Patent Application No. PCT/US2020/013388, mailed on Jul. 29, 2021, 9 pages.

International Search Report and Written Opinion for PCT application No. PCT/US2020/013309, mailed on May 8, 2020, 13 pages.

Jones et al., "Mycelium Composites: A Review of Engineering Characteristics and Growth Kinetics", Journal of Bionanoscience, vol. 11, No. 4, ISSN: 1557-7910, DOI:10.1166/jbns.2017.1440, Aug. 1, 2017, pp. 241-257.

Schmitt et al., "Are These baked Mushroom Sandals the Future of Fashion", Smithsonian Magazine Website, Available Online at: < https://www.smithsonianmag.com/science-nature/are-baked-mushroom-shoes-futureashion-180969152/>, May 23, 2018, 3 pages.

Tang et al., "Mycelium Afoot: Fashioning Sustainable Footwear", Proceedings of the International Textile and Apparel Association (ITAA); Cleveland Ohio, Jan. 1, 2018, 4 pages.

Better Shoes Foundation : Material Selection, Available online at<https://www.bettershoes.org/home/material-selection>, 2018, pp. 1-17.

Non-Final Office Action received for U.S. Appl. No. 16/741,080, mailed on Sep. 20, 2022, 13 pages.

Redefining Leather with Mycelium, Mycoworks, Available online at <https://web.archive.org/web/20170425115842/http://www.mycoworks.com//#qualities>, 2017, pp. 1-10.

UD Researchers Developing Eco-friendly Shoe Soles Out of Mushroom Roots, Delaware Science, Health, Tech, Available online at <https://www.delawarepublic.org/science-health-tech/2018-04-06/ud-researchers-developing-eco-friendly-shoe-soles-out-of-mushroom-roots>, Apr. 6, 2018, pp. 1-3.

Camere et al., "Growing Materials for Product Design", In Alive. Active. Adaptive: Proceedings of International Conference on Experiential Knowledge and Emerging Materials (EKSIG), Jun. 2017, pp. 101-115.

The Engineering ToolBox (2004), "Friction—Friction Coefficients and Calculator", 11 Pages. [online] Available at:https://www.engineeringtoolbox.com/friction-coefficients-d_778.html [Accessed Jun. 29, 2023.

TheMatWeb Logo (1996-2023), "Overview of materials for Thermoplastic Polyurethane (TPUR), Polyether Grade". 3 Pages [online] Available at:https://www.matweb.com/search/datasheet.aspx?matguid=b4c5102d22ef42758ad6888c9cd34dd9&n=1&ckck=1.

Final Office Action received for U.S. Appl. No. 16/741,080, mailed on May 23, 2023, 14 pages.

Non-Final Office Action received for U.S. Appl. No. 16/741,080, mailed on Dec. 29, 2023, 11 pages.

Final Office Action received for U.S. Appl. No. 16/741,080, mailed on May 3, 2024, 12 pages.

\* cited by examiner

BIOCOMPOSITE MATERIAL AND METHOD FOR FORMING A BIOCOMPOSITE MATERIAL

CROSS REFERENCE TO RELATED APPLICATIONS

The present application claims priority to U.S. Provisional Patent Application No. 62/792,784, entitled "BIOCOMPOSITE MATERIAL AND METHOD FOR FORMING A BIOCOMPOSITE MATERIAL" and filed Jan. 15, 2019. The entire contents of the above-listed application are incorporated herein by reference for all purposes.

BACKGROUND

Wearable articles may include components that are manufactured separately and coupled together using stitching or other fastening mechanisms. The components of the wearable article may be made out of leather, polyurethane, and/or other materials that may have lengthy manufacturing times and may not be biodegradable.

SUMMARY

In one example, a biocomposite material includes a biopolymer material and an internal structure imparting zonal properties to the biocomposite material, where the biopolymer material at least partially surrounds and/or extends through the internal structure. The biopolymer material includes mycelium grown from a fungal strain.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1:
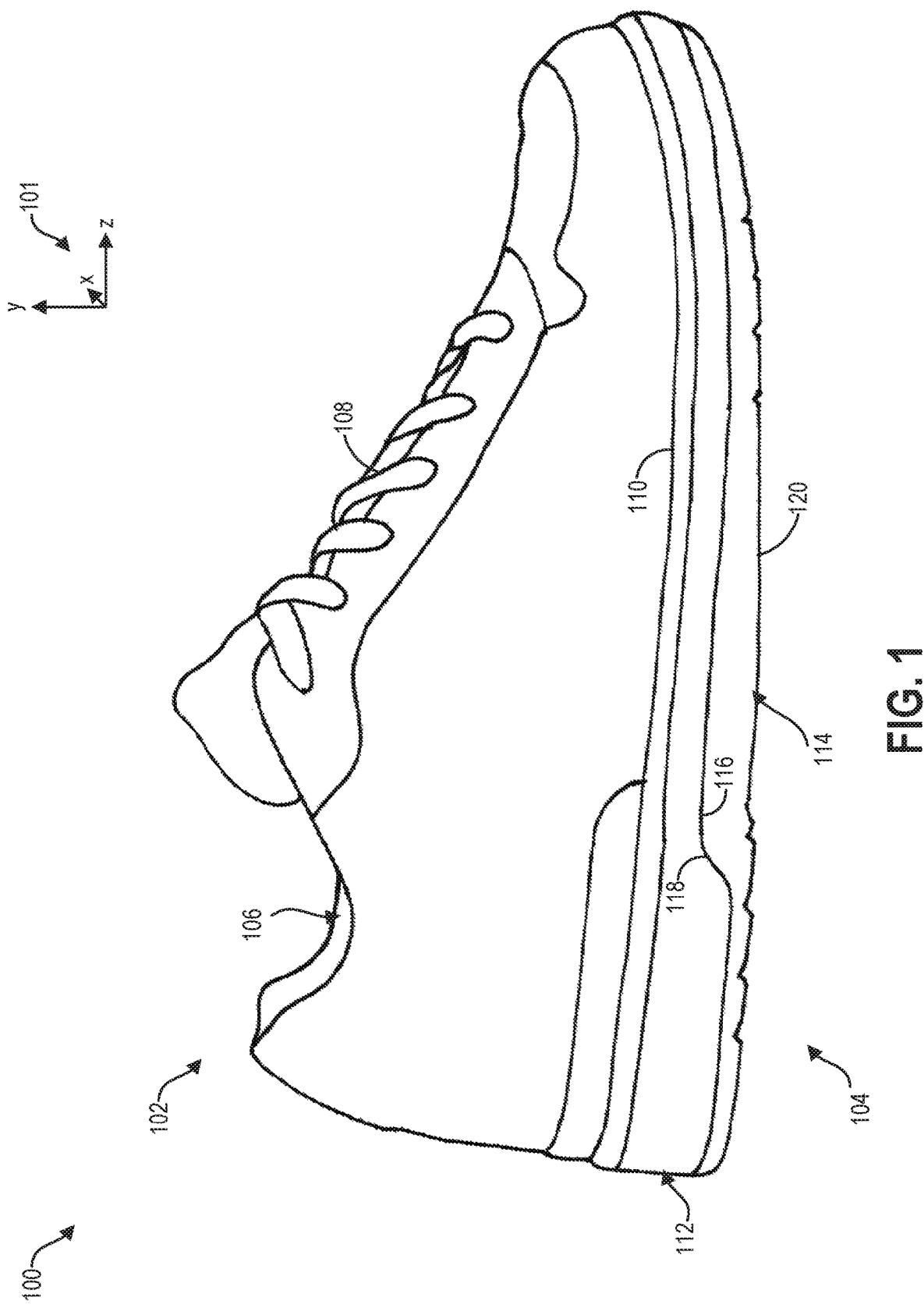
FIG. 1 shows an example of a wearable article in the form of a shoe with an upper and a sole structure.

The following description relates to a biocomposite material, wearable articles, and methods for manufacturing wearable articles, and in one example, footwear and methods for manufacturing footwear. In particular, the following description relates to wearable articles manufactured from biocomposite material comprised of biological polymers grown in and/or cut to the shape(s) of the wearable article. The biological polymers may be grown around an inner structure that has zoned properties, such as zones that are more or less rigid, zones that are more or less cushioned, and so forth. The biological polymers may mimic the properties of the inner structure, resulting in a wearable article having desired zoned material properties.

Typically, wearable articles, such as footwear, may be manufactured by separately manufacturing the article components (e.g., the upper and the sole in the example of footwear) and then joining the separate components together. Further, each of the components may be formed from separate pieces that may be manufactured independently of each other and then joined together. This separate manufacturing and then joining together of multiple components may result in complex manufacturing processes that cannot be easily scaled up or scaled down as demand for the final wearable article product fluctuates. Further, this manufacturing process may involve extensive manual input, which may lead to a more costly and lengthy manufacturing process. Furthermore, many wearable articles are manufactured from materials that are essentially not degradable and/or that release harmful byproducts during the degradation process. Additionally, the wearable materials may be generated using environmentally-unfriendly compounds.

Thus, according to embodiments disclosed herein, the above issues may be addressed by forming a wearable article from biocomposite materials comprised of biological polymers grown in the shapes of the various wearable article components. The biocomposite materials may be biodegradable and may rely on little or no harmful chemicals to produce. Further, the biocomposite materials may be grown quickly, such as within a few days or weeks, relative to other materials, which take months or even years to produce. Further still, at least in some examples, some or all of the wearable article components may be manufactured using a three-dimensional mold around which the biopolymers may be grown. In this way, the number of separately manufactured components may be reduced, which may reduce the manual input required to produce the wearable article and may allow for easy scaling of the quantity of the wearable articles produced.

While the disclosed embodiments are described herein below in the context of footwear, the biocomposite material disclosed herein may further be equally applied to virtually any article of clothing, apparel, or equipment. For example, the disclosed embodiments may be applied to hats, caps, shirts, jerseys, jackets, socks, shorts, pants, undergarments, athletic support garments, gloves, wrist/arm bands, sleeves, headbands, sports equipment, etc. Thus, as used throughout this disclosure, the term "wearable article" may refer to any apparel or clothing, including any article of footwear, as well as hats, caps, shirts, jerseys, jackets, socks, shorts, pants, undergarments, athletic support garments, gloves, wrist/arm bands, sleeves, headbands, any knit material, any woven material, any nonwoven material, etc. As used throughout this disclosure, the terms "wearable article," "apparel," "article of footwear," and "footwear" may also refer to a textile, a natural fabric, a synthetic fabric, a knit, a woven material, a nonwoven material, a mesh, a leather, a synthetic leather, a polymer, a rubber, and a foam.

Figure 3:
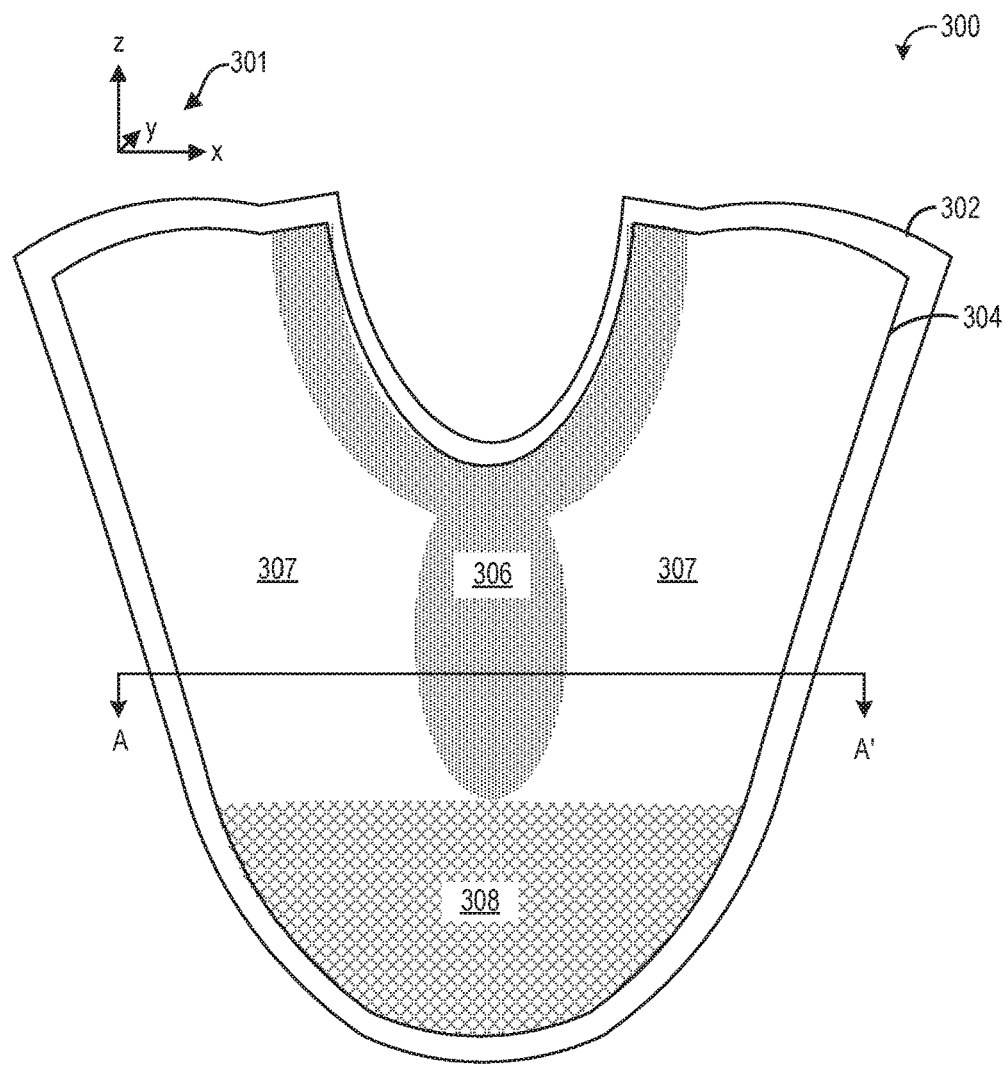
FIGS. 3 and 4 show an example system for generating an upper from a biocomposite material.
Figure 4:
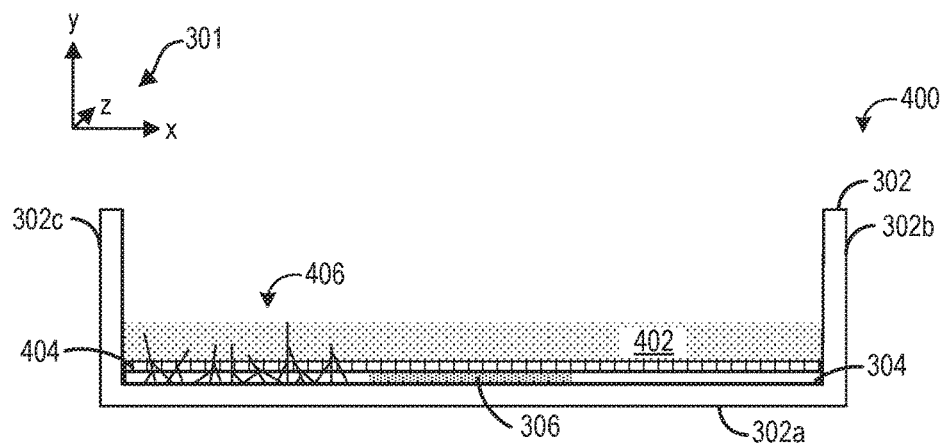
Figure 8:
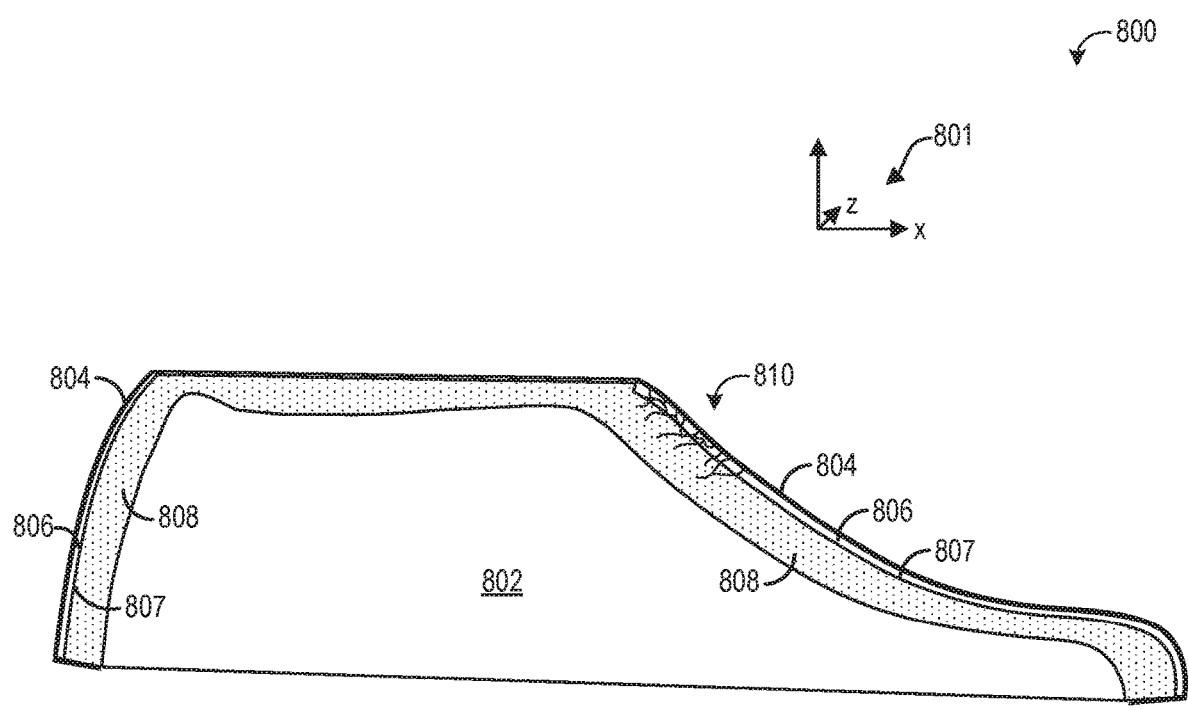
FIG. 8 shows another example system for generating an upper from a biocomposite materials.
Figure 9:
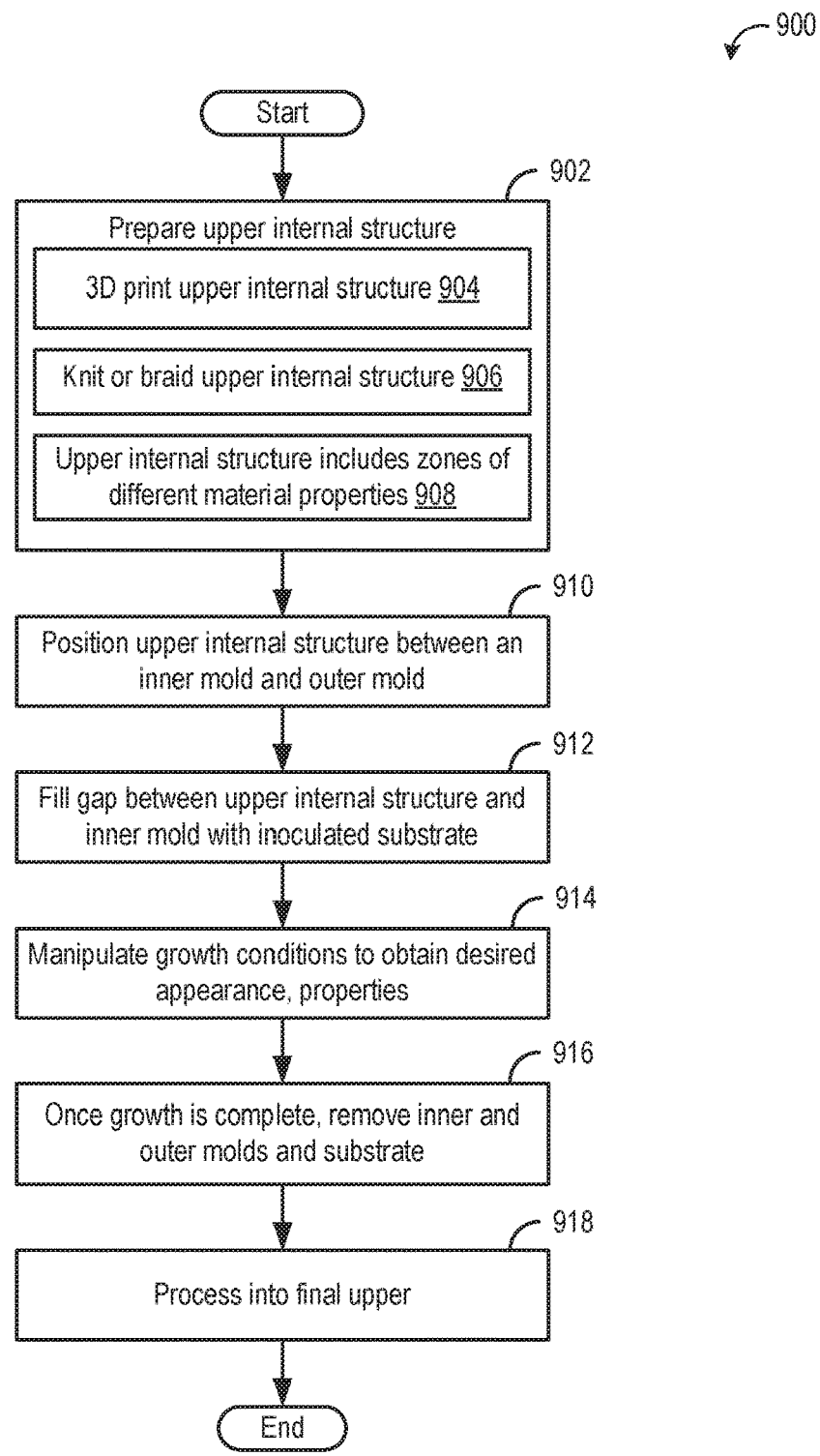
FIG. 9 shows an example of a method for manufacturing an upper using one or more biocomposite materials.

An example of a shoe is shown in FIG. 1. The shoe may include an upper connected to a sole structure. The components of the sole structure, as well as the upper of the shoe is depicted in an exploded view in FIG. 2 to show an ordering and geometry of the shoe elements. One or more components of the footwear may be comprised of a biocomposite material. For example, as shown in FIGS. 3 and 4, an upper of the footwear may be comprised of a biocomposite material that includes a fungal root structure grown around an inner structure (e.g., an upper inner structure). Further, as shown in FIGS. 5A, 5B, 6A, and 6B, a sole of the footwear may be comprised of a biocomposite material that includes a fungal root structure grown around substrate particles and in some examples an inner structure (e.g., a sole inner structure). An example of a method for manufacturing the shoe, including use of one or both of the upper and sole comprised of the biocomposite material, is provided in FIG. 7. As shown in FIG. 8, the upper may be generated from one or more biocomposite materials grown around/within a three-dimensional mold. FIG. 9 shows an example method for manufacturing an upper from a fungal root structure grown around a 3D mold.

Turning now to FIG. 1, an article of footwear is shown. Footwear, and in particular, athletic footwear, may include an upper and a sole structure. While the upper covers a foot and securely positions the foot with respect to the sole structure, the sole structure is positioned under the foot and provides a barrier between the foot and the ground. The sole structure may attenuate ground reaction forces, provide traction and stability, and control foot motion. By attaching the upper to the sole structure to form a shoe, the foot may be surrounded and supported by the shoe so that the wearer may comfortably participate in recreational activities, such as walking and running.

Accordingly, FIG. 1 shows a shoe 100 that may comprise an upper 102 and a sole structure 104. A set of reference axis 101 is provided, indicating a y-axis, an x-axis, and a z-axis. The upper 102 may be arranged above the sole structure 104 and adapted to allow a foot to be inserted into a cavity of the shoe 100 through an opening 106. The foot is held in place in the shoe 100 by the upper 102 and may directly contact inner surfaces of the upper 102. To provide comfortable engagement of the foot with the upper 102, the upper 102 may be constructed from a flexible synthetic material, such as polyester, nylon, synthetic leathers, or a natural material such as leather; or the upper may be constructed from a biocomposite material as will be explained in more detail below with respect to FIGS. 3 and 4. The shoe 100 may further include a sock liner arranged along an inner surface of the upper 102, inside the cavity of the shoe, and attached to the upper 102 by stitching.

The upper 102 may be adapted with a lacing system 108 including a set of laces threaded through apertures in the upper 102 along a region of the upper 102 adjacent to an instep of the foot when the shoe 100 is worn. In other examples, the upper 102 may have a Velcro attachment instead of the lacing system 108 or neither the lacing system 108 nor the Velcro attachment. The lacing system may be used to tighten the upper around the foot and enhance a securing of the foot inside the shoe 100.

The upper 102 may be secured along a bottom edge 110 to the sole structure 104. The sole structure may include an insole positioned inside the cavity of the shoe 100 along a footbed of the shoe, a midsole 112, and an outsole 114. The midsole 112 is directly adjacent to and above the outsole 114 so that the midsole 112 and the outsole 114 are in face-sharing contact, the shared face coplanar with an x-z plane. The midsole 112 may be a compressible layer of a foamed material, such as ethylene vinyl acetate (EVA), polyurethane (PU) or thermoplastic polyurethane (TPU). As described above, midsole 112 is configured to attenuate ground forces and decrease impact transferred to the foot due to contact of the shoe with the ground. In some examples a thickness, defined along the y-axis, of the midsole 112 may vary according to a desire for increased shock absorption at certain regions relative to the foot. For example, a region under a heel of the foot may be thicker than a region under a ball of the foot if the shoe 100 is adapted for long distance running. In addition, a firmness of the midsole 112 may be non-uniform along the midsole 112 to provide stability or cushioning in desired regions of the midsole 112.

The outsole 114 may have an upper face 116 that is contoured to match a bottom face 118 of the midsole 112. A bottom face 120 of the outsole 114 may be textured to provide traction to the shoe 100. The outsole 114 may be formed from a material that is less compressible and more durable than the midsole 112, such as carbon rubber or blown rubber, or the outsole may be formed from a biocomposite material as will be explained below.

Figure 2:
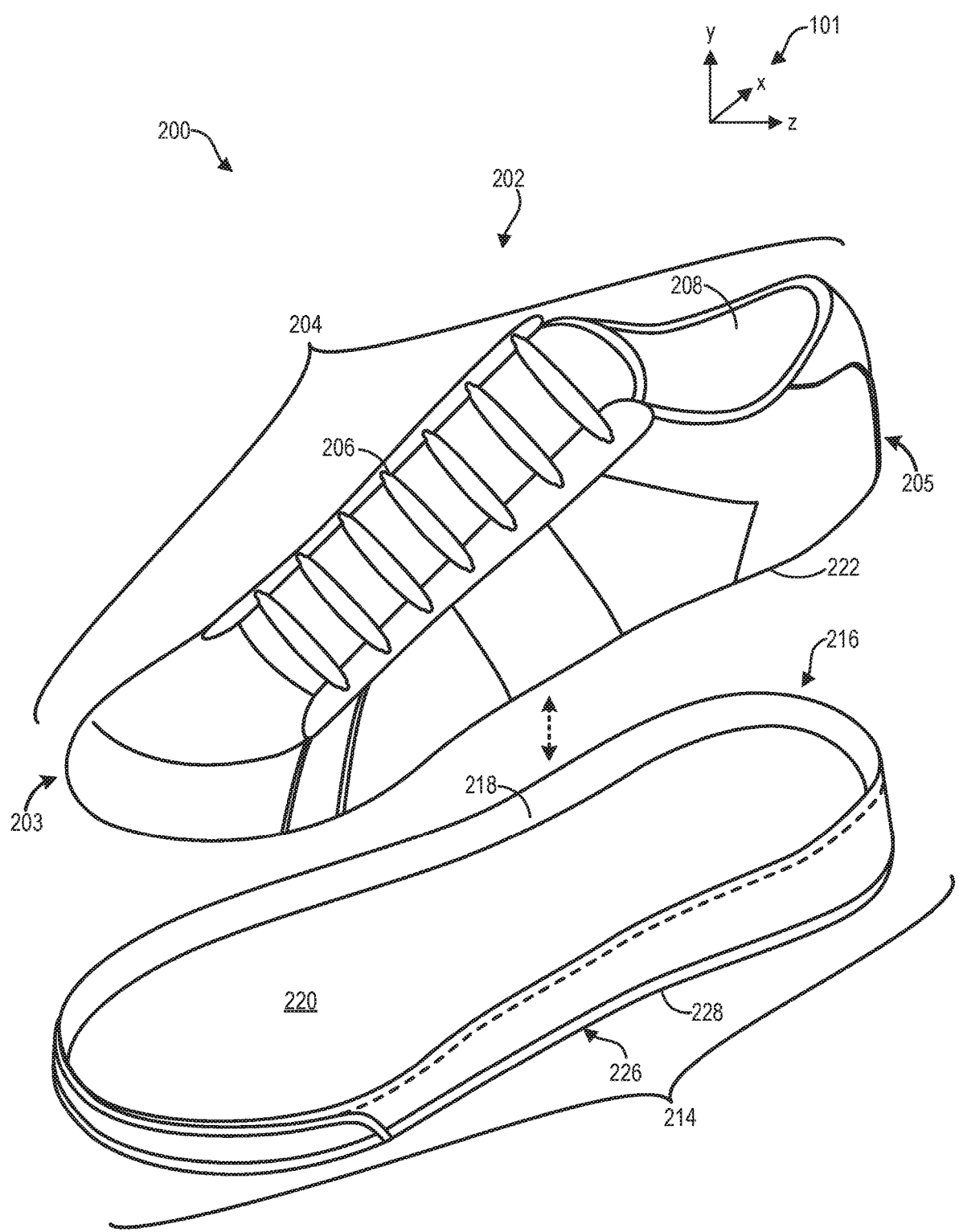
FIG. 2 shows an exploded view of an example of a shoe.

The components of a shoe 202 are shown in an exploded view 200 in FIG. 2. The shoe 202 has a toe region 203 and a heel region 205 and comprises an upper 204 with a lacing system 206 and an opening 208 as well as a sole structure 214 that includes a midsole 216 and an outsole 226. The upper 204 may have an attached sock liner (not shown in FIG. 2) that lines an interior of the upper or the upper may be directly stitched to a seamed footbed that provides a bottom surface to the upper 204. Furthermore, in some examples, the sole structure 214 may also include an insole positioned below the upper 204 and above the midsole 216 that is contoured to match a shape of a foot. The insole may be arranged above the sock liner or the seamed footbed at a bottom of an inner cavity of the shoe 202 and may be formed from EVA or other material.

The sole structure 214 may be shaped to match an outer geometry of a bottom edge 222 of the upper 204. The midsole 216 may have a raised edge 218 surrounding at least a portion of a perimeter of the midsole 216 that extends above an upper surface 220 of the midsole. A width of the midsole 216, defined along the x-axis, may be wider than a width of the upper 204 and the insole 210 so that the bottom edge 222 of the upper 204 may fit within and be surrounded by the raised edge 218 of the midsole 216.

Portions of the outsole 226 in FIG. 2 may be similarly shaped as the midsole 216 but the outsole 226 may alternatively comprise a plurality of sections that are fixed to regions of a bottom surface of the midsole 216. The outsole 226 may be adapted to provide traction in desirable regions of the sole structure 214, such as under a ball of the foot. The outsole 226 may be thinner, as defined along the y-axis, than the midsole 214. The outsole 226 may be contoured to match a shape of the midsole 216 and include a textured bottom face 228.

At least some of the components of shoe 202 may be comprised of a biopolymer material that is biodegradable. For example, as will be described in more detail below, one or more of an upper and a sole portion of a shoe may be manufactured from fungal root structure, referred to as mycelium. Mycelium is comprised of a plurality of branching, thread-like filaments, referred to as hyphae, that secrete enzymes into a food source, such as wood. The enzymes break down polymers in the food source into monomers that are absorbed into the hyphae and supplied to the fungus. The branching and thread-like nature of the mycelium hyphae may result in the formation of a flexible, durable material that can be processed and utilized in a desired manner.

To generate an upper made from mycelium, the mycelium may be grown in a tray that has the shape of an upper, and may be encouraged to grow in such a manner that different material properties of different portions of the upper may be mimicked in the mycelium. To accomplish this, the mycelium may be grown around an internal structure, such as fabric, polylactic acid (PLA), or other biodegradable material that includes desired material properties (e.g., more or less stretchable in certain regions, more or less rigid in other regions, and so forth), and the mycelium may grow around and through the textile, which may cause the mycelium to have a density, a growth direction, etc., that causes the grown mycelium to mimic the material properties of the textile. To generate a sole portion from mycelium, the mycelium may be grown around an internal structure and at least in some examples, in a tray that has the shape of the sole. The internal structure may include zones of different material properties, such as a rigid arch support, flexible/compressible heel region, and so forth. To form an open or closed cell foam-like material, the mycelium may be grown around small, dispersed pieces of substrate, thereby generating a foam-like structure that has the shock absorbing and other material properties typically associated with a sole. Once the upper and sole are manufactured, the upper and sole may be coupled together into a shoe via stitching or other fastening mechanisms.

By manufacturing one or more portions of a shoe using mycelium, production of the shoe may be easily and quickly scaled up or scaled down depending on demand, and the amount of manual effort required to manufacture the shoe may be reduced. Further, the one or more portions made from mycelium may be biodegradable, and the process of growing and processing the mycelium into the portions of the shoes may utilize fewer chemicals that may be harmful for the environment relative to manufacturing the portions from petrochemicals such as polyurethane.

FIG. 3 shows a top-down view of an example system 300 for manufacturing an upper, with some of the components of system 300 (e.g., the substrate and intermediate layer) removed for visual purposes to highlight the zoned properties of the upper internal structure. FIG. 4 shows a cross-sectional view 400 of the system 300 taken across line A-A' of FIG. 3, with the components of the system shown. Each of FIGS. 3 and 4 includes a coordinate system 301. FIGS. 3 and 4 will be described collectively. System 300 is configured to generate an upper for incorporation in an article of footwear, such as a shoe. For example, upper 102 of FIG. 1 and/or upper 204 of FIG. 2 may be formed using system 300.

System 300 includes a tray 302. Tray 302 may be comprised of a suitable material, such as plastic or other substance adapted for culturing cells, bacteria, and/or mycelium. Tray 302 is configured to minimize opportunities for infection and allow for the control of environmental factors such as temperature, humidity, light levels, and CO2 and O2 concentrations. Tray 302 may be configured to control air exchange and O2 and direct the growth of the mycelium to only specific areas through access to atmosphere. For example, tray 302 has a shape that matches the shape of the final upper that is to be produced by system 300 and includes a bottom and sides, such as bottom 302a, first side 302b, and second side 302c.

System 300 further includes an upper internal structure 304. Upper internal structure 304 may extend in the x-z plane of FIG. 3 and may be shaped similarly the final shape of the upper that will be produced by system 300, and may be shaped similarly to tray 302. In some embodiments, upper internal structure 304 may be positioned directly on tray 302 without any material positioned intermediate upper internal structure 304 and tray 302. Upper internal structure 304 may be comprised of a suitable biodegradable material or materials, such as PLA, fabric, and/or other material(s), and may be woven, braided, knitted, 3D printed, or made in another suitable manner. Further, in some examples, upper internal structure 304 may be comprised of multiple pieces of material which may be maintained separate or may be stitched, fused, or otherwise fastened together, or upper internal structure 304 may be comprised of a single, unitary piece of material. Upper internal structure 304 may be permeable to mycelium growth such that hyphae 406 (shown in FIG. 4 and described in more detail below) growing down from substrate 402 may grow through and around upper internal structure 304.

The inclusion of upper internal structure 304 may cause the final upper produced from system 300 to have desired material properties. For example, upper internal structure 304 may cause the final upper to be more rigid, more flexible, etc., than if the mycelium were grown without an upper internal structure. Upper internal structure 304 may influence the growth pattern (e.g., density, hyphae growth direction, hyphae branching directionality, and so forth) of the mycelium. For example, if upper internal structure 304 is stretchable in a first direction, the resulting mycelium may also be stretchable in the first direction. Thus, to encourage specific material properties of the final upper, upper internal structure 304 may include regions or zones having different material properties. As shown, upper internal structure includes a lacing zone 306, toe zone 308, and side zones 307. Lacing zone 306 may be configured to accommodate a lacing system that may be incorporated after the final upper is produced. It may be desirable for lacing zone 306 to have more elasticity than other zones of the upper, and thus upper internal structure 304 may be more elastic in lacing zone 306 than in other zones of upper internal structure 304. Toe zone 308 may be configured to be placed over a toe of a wearer when the final upper is incorporated into a shoe. It may be desirable for toe zone 308 to be comprised of material having a higher density than other regions of the upper, or it may be desirable for toe zone 308 to be made of mesh-like material. Thus, toe zone 308 may be comprised of a higher density material than other regions of upper internal structure 304 or have otherwise different material properties than remaining portions of upper internal structure 304. It is to be understood that the above described zones of upper internal structure 304 are exemplary, and other regions are possible, having the same or different material properties than those described above. Further, in some examples, the upper internal structure may be comprised of material having the same material properties in all zones, or the upper internal structure may be omitted.

The sides of tray 302 may enclose substrate 402, on which the mycelium may grow (the mycelium is comprised of branching hyphae 406, growing outward and downward from substrate 402 in FIG. 4). The bottom and sides of tray 302 may constrain the growth of the mycelium such that the mycelium grows downward from the substrate 402 to the bottom 302a of the tray 302. Once the mycelium growth reaches the bottom of the tray, the mycelium may grow to form a "skin" in and around internal structure 304, and the resultant mycelium-internal structure composite material may then be harvested and processed to form an upper, as will be described in more detail below.

Substrate 402 may include nutrients that allow the desired fungi strain to grow over a period of time by digesting the nutrients. Substrate 402 may be comprised of any material adequate to provide for the growth of the fungal material. Substrate 402 may be a ligno-cellulosic material with appropriate pH balance and other nutrients commensurate for the propagation of a desired fungal strain. For example, substrate 402 may be solid wood or wood particles.

Substrate 402 may be inoculated with an appropriate fungal strain. The fungal species may be from the fungal kingdom order Polyporales, the Family Ganodermataceae, such as *Ganoderma lucidum, Ganoderma tsugae, Ganoderma applanatum, Ganoderma resinaceum*, or *Ganoderma oregonense*. Other possible candidate strains include *Trametes versicolor, Trametes pubescens, Schizophyllum commune*, and *Polyporous squamosus*. The desired fungal strain is propagated throughout substrate 402 so that the substrate is fully colonized by the fungal mycelium.

Substrate 402 may fill tray 302 across an entirety of tray 302 in the x-z plane (e.g., across an entirety of tray 302), and may extend at least partially up the sides of tray 302 (e.g., along the y axis). Substrate 402 may have a flat bottom surface, to encourage straight and consistent growth, or substrate 402 may have a bottom surface of desired contours and/or curvature.

Upon mycelium growth, upper internal structure 304 may be incorporated into an intermediate region of the final upper, such that one or more layers of mycelium are present below upper internal structure 304 and one or more layers of mycelium are present above upper internal structure 304. For example, as shown in FIG. 4, hyphae 406 may grow through and around upper internal structure 304. It is to be understood that hyphae 406 are shown in schematic form for visual purposes, and that hyphae 406 may grow across the entirety of substrate 402 (only a portion of the hyphae is shown for clarity) and hyphae 406 may take on other visual appearances, densities, growth directions, etc.

During hyphae growth, the conditions surrounding and/or within tray 302 may be controlled to generate desired properties of the resultant mycelium. For example, a lid may be placed on tray 302 to control air exchange, limit light exposure, etc. The air in and/or surrounding tray 302 may be controlled to have a specific O2 and/or CO2 content, temperature, and/or humidity, which may all affect the growth properties of the hyphae. The growing hyphae may be manipulated directly, such as by mechanical pressure, deformation, chemical growth promotors or inhibitors, and so forth.

In some embodiments, an intermediate layer 404 may be positioned on top of upper internal structure 304 and below substrate 402. Intermediate layer 404 is configured to physically isolate the growing fungal material from the substrate 402. Intermediate layer 404 may be a membrane or fabric that is permeable to the growing fungal material but not to the particles of the substrate. Intermediate layer 404 may enable uniform growth of the fungal material by providing uniform initial conditions of growth and enables the fungal material to be cleanly removed without damaging the substrate during a delamination process after desired fungal growth is complete.

Intermediate layer 404 facilitates uniform separation of the fungal material from the substrate by controlling the interaction of the substrate with the fungal material. Thus, intermediate layer 404 prevents the fungal material from permanently adhering to the substrate, and damaging or tearing of the substrate when removing the fungal material. The substrate can thus be reused to grow additional mycelial structures. Intermediate layer 404 may be fully or partially permeable across its surface. Growth of fungal material will be blocked in impermeable areas, allowing for masked or patterned growth. For example, while not shown in FIG. 3, it may be desirable to include openings within the final upper to accommodate laces or other shoe fasteners (e.g., hook-and-loop fasteners), and thus intermediate layer 404 may include impermeable areas corresponding to the final location of the openings (likewise, in such examples, upper internal structure 304 may include voids where openings in the final upper are desired).

In some embodiments, the intermediate layer is a stand-alone component separate from the tray and the substrate. In other embodiments, the intermediate layer is attached to or is permanently a part of the tray, or the intermediate layer may be embedded within the substrate. Intermediate layer 404 may comprised of lignin or other biodegradable compounds to interact with the mycelium. In other examples, intermediate layer 404 may be comprised of a polymer that is not degraded by the fungi.

Once the mycelium has grown to a desired thickness, the mycelium and incorporated upper internal structure 304 may be removed from substrate 402 and intermediate layer 404 via a delamination process. The resultant composite upper material comprised of the mycelium and upper internal structure may then be processed via a suitable tanning or other process to ensure the composite upper material is water resistant, shielded from mycelium degradation, and/or other desired properties. Further, the composite upper material (e.g., comprised of mycelium and the upper internal structure) may be trimmed, folded, and/or manipulated to include a lacing system, tongue, and/or other components, to thereby form an upper comprised of a biocomposite material. The upper may be incorporated into an article of footwear, such as shoe. For example, the upper may be stitched to a sole portion, may be modified to include a lacing system (if not yet added), and so forth.

Additionally, while upper internal structure 304 is shown in FIGS. 3 and 4 as extending across an entirety of tray 302, such that all portions of the resultant upper include the upper internal structure, in some examples the upper internal structure may be of a different shape, comprised of different, unconnected (or only partially connected) regions, include voids or cut-outs, etc., such that some regions or zones of the resultant upper do not include an upper internal structure but instead are only comprised of the mycelium.

Thus, system 300 may be utilized to generate an upper to be incorporated into an article of footwear. The upper may be comprised of a biocomposite material. The biocomposite material may include a biopolymer, herein mycelium that is grown from a suitable fungal strain, and an internal structure. The inclusion of the internal structure may result in the upper having zonal properties. The zonal properties may include some regions/zones of the upper having different properties than other regions/zones of the upper. For example, when upper internal structure 304 is included in an upper, the upper may have a toe zone and a lacing zone, each of which may have different density, thickness, and/or material properties than other regions (e.g., the sides) of the upper. The different material properties may include different elasticity, different compressibility, etc. Further, the biocomposite material that is formed from system 300 may be processed similar to leather and may result in a material that is similar in some properties as leather. As such, the biocomposite material may be dyed, perforated, laser etched, embossed, debossed, etc.

While system 300 is described above as being configured for forming an upper for an article of footwear, a similar system may be used to generate other wearable articles. For example, a hat, gloves, shirt, pants, socks, etc., may be formed using a system that includes a tray (which may be in the shape of the wearable article), an internal structure, and a substrate inoculated with a fungal strain. Upon mycelium growth from the fungal strain, one or more layers of mycelium may grow over, under, and/or through the internal structure to form a biocomposite material having zonal properties, where the zonal properties include zones with the internal structure and the mycelium, and zones without the internal structure and only the mycelium, and/or where the zonal properties include the internal structure having zones/regions of different density, thickness, material properties, etc. Further, while system 300 includes a tray that has the same shape as the final upper that is formed using system 300, in some examples the system may include a tray having a different shape. For example, the tray may be rectangular and the upper (or other wearable article) may be cut from the tray after mycelium growth is complete.

Figure 5A:
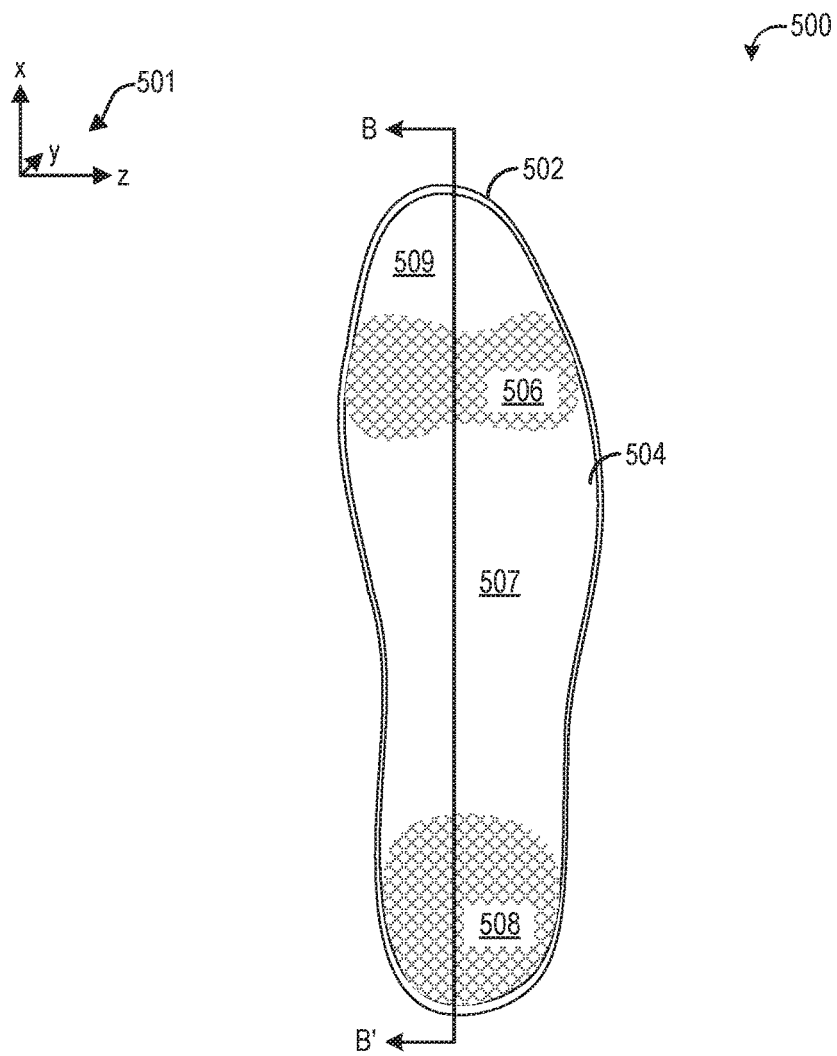
FIGS. 5A and 6A show a first example system for generating a sole from a biocomposite material.
Figure 6A:
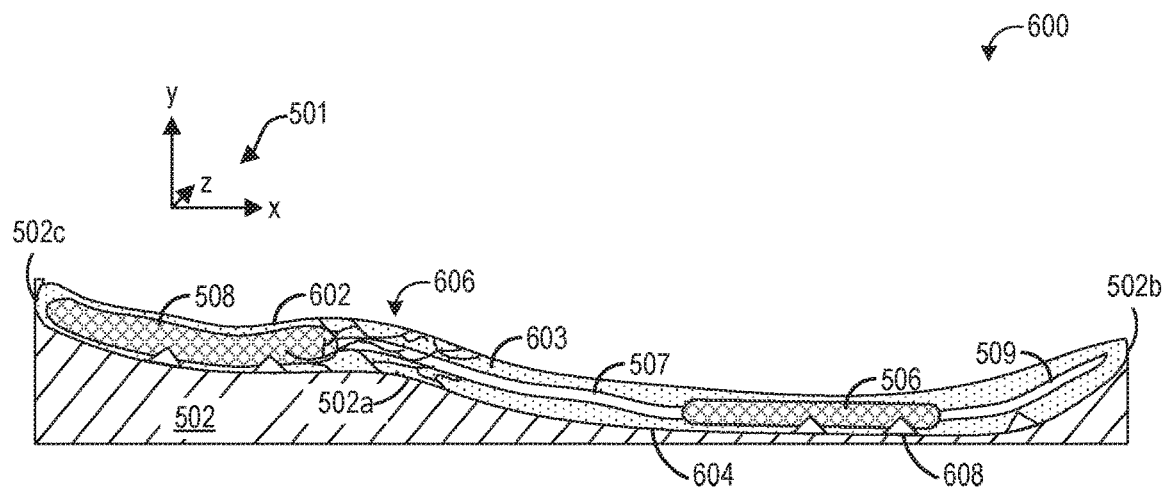

In some examples, the sole portion of an article of footwear, such as some or all of sole structure 104 of FIG. 1 and/or some or all of sole structure 214 of FIG. 2, may be comprised of a biodegradable material (e.g., mycelium) grown from a substrate inoculated with a fungal strain. FIGS. 5A and 6A show a first example system 500 for manufacturing a sole. FIG. 5A shows a top-down view of system 500 with some components (e.g., the substrate and top surface) removed for visual purposes. FIG. 6A shows a cross-sectional view 600 of the system 500 taken across line B-B' of FIG. 5A with the substrate and top surface included. Each of FIGS. 5A and 6A includes a coordinate system 501. FIGS. 5A and 6A will be described collectively. System 500 is configured to generate a sole for incorporation in an article of footwear, such as a shoe. For example, some or all of sole structure 104 of FIG. 1 and/or some or all of sole structure 214 of FIG. 2 may be formed using system 500. Further, in some examples, both the midsole and the outsole of the sole structure may be formed using system 500. In other examples, only the midsole or only the outsole of the sole structure may be formed using system 500.

System 500 includes a tray 502. Tray 502 may be comprised of a suitable material, such as plastic or other substance adapted for culturing cells, bacteria, and/or mycelium. Further, tray 502 may provide for sterile conditions and/or may allow for air exchange, similar to tray 302 described above. Tray 502 has a shape that matches the shape of the final sole formed using system 500 and includes a bottom and sides, such as bottom 502a, first side 502b, and second side 502c.

System 500 further includes a sole internal structure 504. Similar to upper internal structure 304, sole internal structure 504 may cause the final sole produced from system 500 to have desired material properties. For example, sole internal structure 504 may cause the final sole to be more rigid, more flexible, more compressible, etc., than if the mycelium were grown without a sole internal structure. Sole internal structure 504 may influence the growth pattern (e.g., density, hyphae growth direction, hyphae branching directionality, and so forth) of the mycelium. For example, if sole internal structure 504 is compressible in a first direction, the resulting mycelium may also be compressible in the first direction. Thus, to encourage specific material properties of the final sole, sole internal structure 504 may include zones having different material properties.

As shown, sole internal structure 504 includes a ball zone 506 configured to be positioned under a ball of a foot when the sole is incorporated into an article of footwear that is worn by a person. Sole internal structure 504 also includes a heel zone 508 configured to be positioned under a heel of a foot when the sole is incorporated into an article of footwear that is worn by a person. Ball zone 506 and/or heel zone 508 may be comprised of a 3-D mesh/grid of material that is compressible in order to facilitate shock absorption, for example. Ball zone 506 and/or heel zone 508 may be comprised of a biodegradable material such as PLA or other suitable material.

Sole internal structure 504 may extend in the x-z plane of FIG. 5A and may be shaped similarly the final shape of the sole that will be produced by system 500, and may be shaped similarly to tray 502. Accordingly, sole internal structure 504 may include a first coupling zone 507 between ball zone 506 and heel zone 508, and in some examples may include a second coupling zone 509 extending from ball zone 506 to the toe edge of the tray 502. The coupling zones may be flexible, rigid, and/or have other desired material properties, and may be comprised of the same material as ball zone 506 and/or heel zone 508, or may be comprised of a different material or materials. In other embodiments, sole internal structure 504 may have a shape that is different than that of the final sole and/or may be comprised of separate, non-contacting zones (e.g., the coupling zones may be dispensed with), as will be explained in more detail below. Sole internal structure 504 may be 3D printed, or made in another suitable manner (e.g., casted, injection molded). Further, in some examples, sole internal structure 504 may be comprised of multiple pieces of material stitched, fused, or otherwise fastened together, or sole internal structure 504 may be comprised of a single, unitary piece of material. In some examples, sole internal structure 504 may be at least partially permeable to mycelium growth such that hyphae 606 (shown in FIG. 6A) growing throughout substrate 603 may grow through and/or around sole internal structure 504.

It is to be understood that the above described zones of sole internal structure 504 are exemplary, and other regions are possible, having the same or different material properties than those described above. Further, in some examples, the sole internal structure may be comprised of material having the same material properties in all zones, or the sole internal structure may be omitted.

The bottom and sides of tray 502 may enclose a substrate 603, on which the mycelium may grow (the mycelium is comprised of branching hyphae 606, growing throughout substrate 603 in FIG. 6A although only a portion of the branching hyphae is shown for clarity). The bottom and sides of tray 502 may constrain the growth of the mycelium such that the mycelium only grows within substrate 603. However, unlike tray 302 which has a substantially flat bottom and flat sides, tray 502 includes varying 3D structure. For example, referring to FIG. 6A, the bottom 502a of tray 502 is not flat, but instead changes in height along the x axis (as shown in FIG. 6A) and/or along the z axis, thereby providing a desired shape to the final sole.

Substrate 603 may include discrete particles and nutrients that allow the desired fungi strain to grow over a period of time by digesting the nutrients, similar to substrate 402. Substrate 603 may be comprised of any material adequate to provide for the growth of the fungal material. Substrate 603 may be a ligno-cellulosic material with appropriate pH balance and other nutrients commensurate for the propagation of a desired fungi strain. However, unlike substrate 402, substrate 603 may include discrete particles, such as saw dust, corn husks, etc., rather than a solid material. The discrete particles may be selected in order to impart desired material properties to the final sole, for example such that the final sole is comprised of a high density foam-like material.

Substrate 603 may be inoculated with an appropriate fungal strain, similar to the fungal strains described above with respect to FIGS. 3 and 4. The fungal species may be from the fungal kingdom order Polyporales, the Family Ganodermataceae, such as *Ganoderma lucidum*, *Ganoderma tsugae*, *Ganoderma applanatum*, *Ganoderma resinaceum*, or *Ganoderma oregonense*. Other possible candidate strains include *Trametes versicolor*, *Trametes pubescens*, *Schizophyllum commune*, and *Polyporous squamosus*. The desired fungal strain is propagated throughout substrate 603 so that the substrate is fully colonized by the fungal mycelium.

Substrate 603 may fill tray 502 across an entirety of tray 502 in the x-z plane (e.g., across an entirety of the bottom of tray 502), and may extend at least partially up the sides of tray 502 (e.g., along the y axis). Substrate 603 may have a flat top surface, to encourage straight and consistent growth, or substrate 603 may have a top surface of desired contours and/or curvature. For example, as shown in FIG. 6A, substrate 603 may be constrained by a top layer 602, which may be included as part of tray 502 or may be a separate component. Top layer 602 may prevent mycelium growth outside of substrate 603, while still allowing for exchange of light, air, etc. In other examples, top layer 602 may allow growth of the mycelium above substrate 603, but may facilitate removal of the mycelium that grows above substrate 603, such that the final sole has the shape shown in FIG. 6A.

In some examples, system 500 includes an intermediate layer 604 positioned underneath substrate 603, in between substrate 603 and tray 502. Intermediate layer 604 may facilitate removal of the substrate-mycelium structure from tray 502 once desired mycelium growth has been achieved and/or may act as a durable outer surface for the sole once mycelium growth is complete. However, in some examples, intermediate layer 604 may be dispensed with, as the tray itself may allow for easy removal of the substrate-mycelium structure. Further, in some examples, one or more tread molds, such as tread mold 608, may be positioned under substrate 603. The tread molds may prevent mycelium growth and substrate deposition in regions of the sole where a tread pattern may be desired.

During hyphae growth, the conditions surrounding and/or within tray 502 may be controlled to generate desired properties of the resultant mycelium. For example, a lid may be placed on tray 502 to control air exchange, limit light exposure, etc. The air in and/or surrounding tray 502 may be controlled to have a specific O2 and/or CO2 content, temperature, and/or humidity, which may all affect the growth properties of the hyphae. The growing hyphae may be manipulated directly, such as by mechanical pressure, deformation, chemical growth promotors or inhibitors, and so forth.

Once the mycelium has grown to a desired thickness, the mycelium and incorporated substrate and sole internal structure (which may be referred to as a composite sole material) may be removed from tray 502. The composite sole material may then be processed via a suitable process to ensure the composite sole material is water resistant, shielded from mycelium degradation, and/or other desired properties. The composite sole material may be incorporated into an article of footwear, such as shoe. For example, the composite sole material may be stitched to an upper, may be modified to include treads or other patterns, and so forth.

Figure 5B:
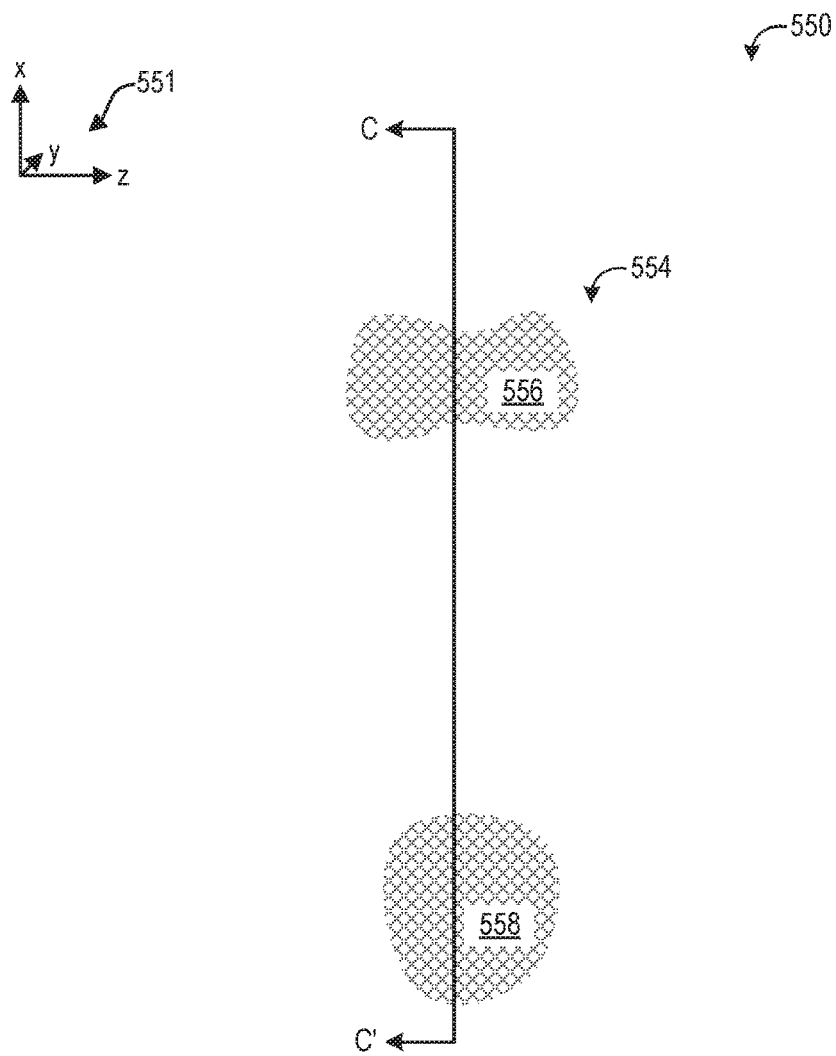
FIGS. 5B and 6B show a second example system for generating a sole from a biocomposite material.
Figure 6B:
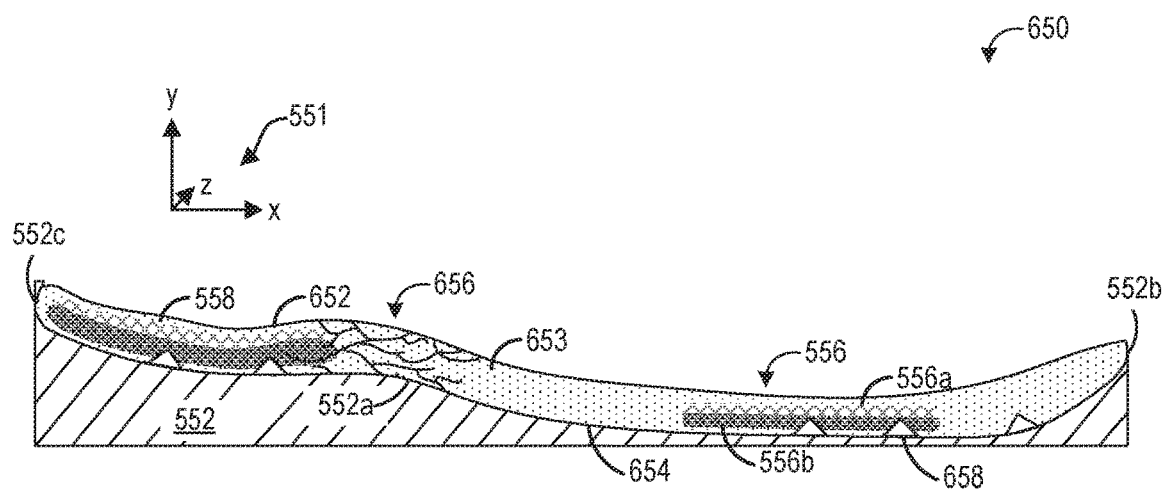

FIG. 5B shows a top-down view of system 550 with some components (e.g., the substrate and top surface) removed for visual purposes. FIG. 6B shows a cross-sectional view 650 of the system 550 taken across line C-C' of FIG. 5B with the substrate and top surface included. Each of FIGS. 5B and 6B includes a coordinate system 551. FIGS. 5B and 6B will be described collectively. System 550 is configured to generate a sole for incorporation in an article of footwear, such as a shoe. For example, some or all of sole structure 104 of FIG. 1 and/or some or all of sole structure 214 of FIG. 2 may be formed using system 550. Further, in some examples, both the midsole and the outsole of the sole structure may be formed using system 550. In other examples, only the midsole or only the outsole of the sole structure may be formed using system 550.

System 550 includes similar components as system 500, including a tray 552 that has a shape that matches the shape of the final sole formed using system 550 and includes a bottom and sides, such as bottom 552a, first side 552b, and second side 552c. System 550 further includes a substrate 653, which may be similar to substrate 603, a top layer 652, an intermediate layer 654, and a tread mold 658 similar to system 500. Thus, description of these components provided above with respect to FIGS. 5A and 6A likewise applies herein.

System 550 further includes a sole internal structure 554. Similar to upper internal structure 304 and sole internal structure 504, sole internal structure 554 may cause the final sole produced from system 550 to have desired material properties. As shown, sole internal structure 554 includes a ball zone 556 configured to be positioned under a ball of a foot when the sole is incorporated into an article of footwear that is worn by a person. Sole internal structure 554 also includes a heel zone 558 configured to be positioned under a heel of a foot when the sole is incorporated into an article of footwear that is worn by a person. Ball zone 556 and/or heel zone 558 may be comprised of a 3-D mesh/grid of material that is compressible in order to facilitate shock absorption, for example. Ball zone 556 and/or heel zone 558 may be comprised of a biodegradable material such as PLA or other suitable material.

Unlike sole internal structure 504, sole internal structure 554 does not include any coupling zones but instead the ball one 556 and heel zone 558 are discrete components that are not coupled to each other via any other parts of the sole internal structure. In some examples, sole internal structure 554 may be at least partially permeable to mycelium growth such that hyphae 656 (shown in FIG. 6B) growing throughout substrate 653 may grow through and/or around sole internal structure 554. Further, each of ball zone 556 and heel zone 558 may include varying mesh density along a vertical direction (e.g., along the y axis of coordinate system 551). For example, ball zone 556 includes a first layer 556a and a second layer 556b. The first layer 556a may have a lower density than the second layer 556b, e.g., first layer 556a may have a courser grid/mesh with fewer cells and/or larger cells than second layer 556b. In this way, the density of the material comprising the ball zone 556 and heel zone 558 may increase along the y axis, while the compressibility of the material may decrease along the y axis.

It is to be understood that the above described zones of sole internal structure 554 are exemplary, and other regions are possible, having the same or different material properties than those described above. Further, in some examples, the sole internal structure may be comprised of material having the same material properties in all zones, or the sole internal structure may be omitted.

Thus, system 500 and/or system 550 may be utilized to generate a sole to be incorporated into an article of footwear. The sole may be comprised of a biocomposite material. The biocomposite material may include a biopolymer, herein mycelium that is grown from a suitable fungal strain, and an internal structure. The inclusion of the internal structure may result in the sole having zonal properties. The zonal properties may include some regions/zones of the sole having different properties than other regions/zones of the sole. For example, when sole internal structure 504 or sole internal structure 554 is included in a sole, the sole may have a heel zone and a toe zone, each of which may have different density, thickness, and/or material properties than other regions (e.g., the arch) of the sole. The different material properties may include different elasticity, different compressibility, etc. Further, the biocomposite material that is formed from system 500 and/or system 550 may be dyed, perforated, laser etched, embossed, debossed, etc.

Additionally, in some examples, the mycelium that grows in system 500 and/or system 550 may not form a skin. For example, the fungal strain that is inoculated on the substrate in system 500 and/or system 550 may be a different fungal strain than the fungal strain inoculated on the substrate to form the upper as described above with respect to FIGS. 3 and 4. In another example, the growth conditions may be selected to prevent the formation of a skin (e.g., the skin may only form when the mycelium contacts a specific type of surface, which may be omitted from system 500 and/or system 550). In a still further example, a skin may be formed using the system 500 and/or system 550. However, the skin may be removed in one example. In another example, a skin may form and the skin may be maintained in the final sole, which may provide increased durability along the outer surfaces of the sole, for example.

While system 500 and system 550 are described above as being configured for forming a sole for an article of footwear, a similar system may be used to generate other wearable articles. For example, some or all of a hat, gloves, shirt, pants, socks, etc., may be formed using a system that includes a tray (which may be in the shape of the wearable article), an internal structure, and a substrate inoculated with a fungal strain. Upon mycelium growth from the fungal strain, one or more layers of mycelium may be grown over, under, and/or through the internal structure to form a biocomposite material having zonal properties, where the zonal properties include one or more zones with the internal structure and the mycelium and one or more zones without the internal structure and only the mycelium, and/or where the zonal properties include the internal structure having zones/regions of different density, thickness, material properties, etc. Further, while system 500 and system 550 include a tray that has the same shape as the final sole that is formed using the respective system, in some examples the system may include a tray having a different shape. For example, the tray may be rectangular and the sole (or other wearable article) may be cut from the tray after mycelium growth is complete.

In some examples, system 500 and/or system 550 described above may be used to form a midsole. The outsole or the ability to resist an abrasion and also have the proper grip may be incorporated through a different process (e.g., by spraying on a different material, bonding a rubber kind of material at the bottom, etc.). Further, in some examples, rubber particles may be incorporated in the mycelium by including the rubber particles in the substrate, where the particles may get trapped inside the mycelium net in a way that it could give the desired abrasion resistance. Further, the zones of the internal structure having different densities along the vertical direction (e.g., y axis) may likewise be included in an internal structure incorporated into an upper, as described above. Accordingly, in an internal structure incorporated into a biocomposite material configured to form or be incorporated into a wearable article, different zones may be included that have different material properties, and in some examples, the material properties may also vary within a given zone (whether vertically, horizontally, or other manner).

Figure 7:
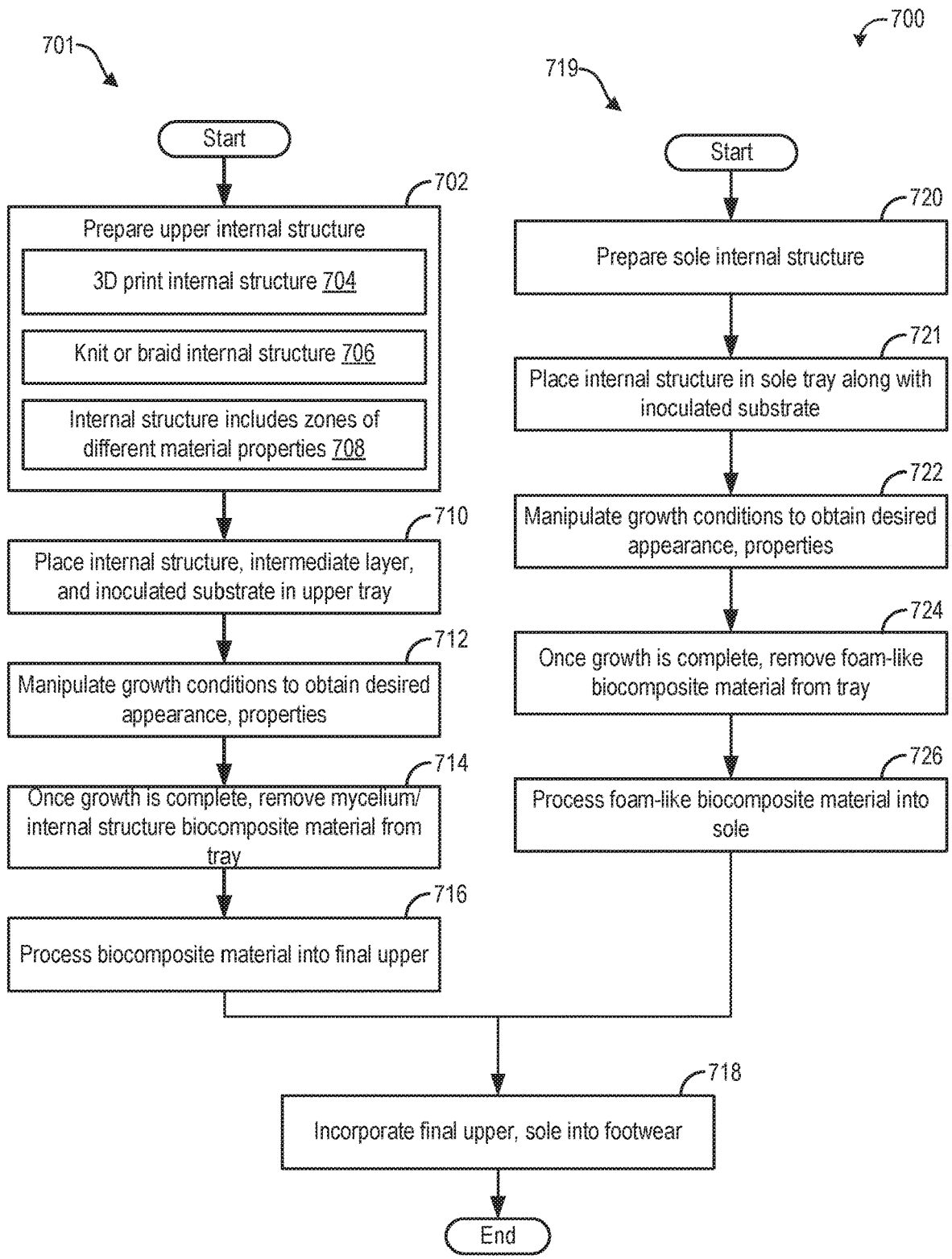
FIG. 7 shows an example of a method for manufacturing a shoe using one or more components comprised of a biocomposite material.

FIG. 7 is a flow chart illustrating a method 700 for manufacturing an article of footwear using one or more components comprised of a biopolymer, such as mycelium. Method 700 may include the manufacture of an article of footwear that includes an upper generated using system 300 described above with respect to FIGS. 3 and 4 and/or a sole generated using system 500 described above with respect to FIGS. 5A and 5B and/or using system 600 described above with respect to FIGS. 6A and 6B. Method 700 includes two branches, a first branch 701 and a second branch 719, which may be performed independently and/or simultaneously. Further, in some examples, the first branch 701 or the second branch 719 may be dispensed with (e.g., and thus only one component of the article of footwear may be comprised of a biopolymer as discussed above).

Referring first to first branch 701 of method 700, an upper internal structure is prepared at 702. The upper internal structure may be similar to upper internal structure 304 described above, and may be generated by 3D printing, as indicated at 704. When the internal structure is 3D printed, the upper internal structure may be comprised of PLA or other biodegradable material that is capable of being 3D printed. In some examples, rather than use a biodegradable material, the upper internal structure may be 3D printed from acrylonitrile butadiene styrene (ABS) or other polymer. However, in other examples, the upper internal structure may be generated by knitting, braiding, weaving, or other techniques, as indicated at 706. For example, the upper internal structure may be comprised of a knit or woven fabric, such as cotton, wool, etc. Additionally, in some examples, the upper internal structure may include zones of different material properties, as indicated at 708. The different material properties may include different materials, different density of material, different thickness of material, different stretch factor of the material, and so forth, as explained above with respect to upper internal structure 304 of FIG. 3.

At 710, the upper internal structure is placed in an upper tray along with an intermediate layer and an inoculated substrate. For example, as explained above with respect to FIGS. 3 and 4, the upper internal structure may be placed into an upper tray, which may be shaped as an upper and may enclose (e.g., on three sides) the inoculated substrate. An intermediate layer may be placed on the upper internal structure and the inoculated substrate may be placed on the intermediate layer.

At 712, the mycelium growth conditions may be manipulated to obtain a desired appearance, material properties, etc., of the resultant mycelium-upper internal structure composite material. The mycelium growth conditions may be manipulated indirectly, such as through ambient conditions (e.g., $O_2$ and/or $CO_2$ content, humidity, supplied nutrients, light, temperature) and/or directly, such as through mechanical pressure, "combing" of the mycelium (e.g., adjusting the directionality of the branching hyphae), voids or antifungal material to inhibit growth in certain regions, and so forth.

At 714, once mycelium growth is complete, the mycelium/upper internal structure biocomposite material is removed from the upper tray. For example, the inclusion of the intermediate layer may allow for the mycelium/upper internal structure biocomposite material to be essentially "peeled" off the substrate without causing damage to the mycelium/upper internal structure biocomposite material or underlying substrate.

At 716, the biocomposite material (e.g., the mycelium/upper internal structure biocomposite material) is processed into a final upper. The processing may include tanning the biocomposite material to remove residual water while preserving the mycelium structure and protecting the biocomposite material from degradation, for example by traditional chrome-based tanning or alternative tanning techniques such as techniques that use aldehydes. The processing may include dying the biocomposite material to achieve one or more desired colors, cutting the biocomposite material to a desired shape and/or to include voids for accommodating laces, perforating, laser etching, embossing, and/or debossing one or more regions of the biocomposite material, and so forth.

At 718, the final upper is incorporated into the article of footwear. For example, the final upper may be coupled to a sole portion. The sole portion may be manufactured from mycelium, as will be explained below with respect to the second branch of method 700, or the sole portion may be manufactured using traditional materials, such as from polyurethane. The final upper may be stitched to the sole portion, the final upper may be placed over an injection cavity and fused to the sole portion during injection molding, or other suitable technique may be employed to join the upper and the sole portion. Method 700 then ends.

Referring next to the second branch 719 of method 700, at 720, a sole internal structure is prepared. Similar to the upper internal structure, the sole internal structure may be 3-D printed using PLA or other material, and/or the sole internal structure may be casted, injection molded, or formed using another suitable technique. Additionally, in some examples, the sole internal structure may include zones of different material properties, where different material properties may include different materials, different density of material, different compressibility factor of the material, different thickness of material, and so forth, as explained above with respect to sole internal structure 504 of FIG. 5A.

At 721, the sole internal structure is placed in a sole tray along with an inoculated substrate. For example, as explained above with respect to FIGS. 5A-6B, a substrate that includes discrete particles, nutrients, and/or other growth material may be inoculated with a desired fungal strain or strains and placed into a sole tray an top of and/or around the sole internal structure, where the sole tray may be shaped as a sole and enclose the inoculated substrate.

At 722, the mycelium growth conditions may be manipulated to obtain a desired appearance, material properties, etc., of the resultant mycelium-substrate composite material. The mycelium growth conditions may be manipulated indirectly, such as through ambient conditions (e.g., O2 and/or CO2 content, humidity, supplied nutrients, light, temperature) and/or directly, such as through mechanical pressure, "combing" of the mycelium (e.g., adjusting the directionality of the branching hyphae), voids or antifungal material to inhibit growth in certain regions, and so forth.

At 724, once mycelium growth is complete, the foam-like mycelium/substrate/internal structure biocomposite material is removed from the sole tray. At 726, the biocomposite sole material (e.g., the mycelium/substrate biocomposite material) is processed into a final sole. The processing may include drying the biocomposite material to remove residual water while preserving the mycelium structure and protecting the biocomposite material from degradation. The processing may include dying the biocomposite material to achieve one or more desired colors, cutting the biocomposite material to a desired shape and/or to include tread patterns, and so forth.

At 718, the final sole is incorporated into the article of footwear. For example, the final sole may be coupled to an upper. The upper may be manufactured from mycelium, as explained above with respect to the first branch of method 700, or the upper may be manufactured using traditional materials. The final sole may be stitched to the upper, or other suitable technique may be employed to join the upper and the sole portion. Method 700 then ends.

Thus, method 700 provides for manufacturing an article of footwear using at least one component comprised of a biopolymer composite material. For example, an upper of the article of footwear may be comprised of a mycelium-internal structure composite material and/or a sole of the article of footwear may be comprised of a mycelium-substrate-internal substrate composite material. The components may be manufactured separately and then coupled together to form the article of footwear. One or more of the internal structures may include zones of different material properties to impart desired structural features to the components. According to the method described above, at least the upper may be formed using a tray, and then the upper may be shaped in a manner to accommodate a foot of a wearer (e.g., by fitting the upper over a last and coupling the upper to a sole).

However, it may be desirable to form the upper using a three-dimensional mold. FIG. 8 shows an example system for manufacturing an upper using a biopolymer that is grown around a 3D mold. FIG. 8 shows a cross-sectional view of a system 800 for forming an upper. FIG. 8 includes a coordinate system 801.

System 800 is configured to generate an upper to form an article of footwear, such as a shoe. For example, the upper of shoe 100 of FIG. 1 and/or shoe 202 of FIG. 2 may be formed using system 800, at least in some examples. System 800 includes an inner mold 802. Inner mold 802 may be a 3D mold in the shape of a foot, similar to a last, and may be comprised of plastic, wood, or other material. Inner mold 802 may be smaller than the desired dimensions of the final upper, in order to accommodate an intermediate layer of substrate, as will be described below. System 800 further includes an outer mold 804. Outer mold 804 may be in the shape of the desired final upper and may have the same dimensions of the desired final upper (or at least substantially the same, such as within 1-5 mm of the dimensions of the desired final upper). Outer mold 804 may be comprised of plastic or other suitable material. For example, the outer mold may be comprised of PLA, PVC, or other thermoplastic that is thermoformed around a mold to form the outer mold in the shape of the upper.

System 800 further includes an upper internal structure 806. Upper internal structure 806 may be similar to upper internal structure 304 of FIG. 3, and as such may be comprised of a biodegradable polymer such as PLA and may be generated by 3D printing, and/or upper internal structure 806 may be comprised of woven, knit, or braided fabric or fibers. Upper internal structure 806 may be comprised of multiple pieces of material, or upper internal structure 806 may be comprised of a single piece of material (e.g., when upper internal structure 806 is 3D printed). Upper internal structure 806 may have a shape and/or varying material properties that match the desired shape and/or material properties of the final upper that will be generated by system 800. For example, upper internal structure 806 may be shaped as an upper when the upper is attached to a sole, and may extend around inner mold 802 in multiple directions (e.g., around sides of inner mold 802, across a back of inner mold 802, and over at least a portion of a top of inner mold 802). Upper internal structure may terminate at a bottom portion of inner mold 802 and may have an opening across a top of inner mold 802 to form the opening to accommodate a foot.

System 800 may further include an intermediate layer 807, which may facilitate easy removal of the upper internal structure/mycelium biocomposite material once desired mycelium growth is achieved. Intermediate layer 807 may be similar to intermediate layer 404 described above with respect to FIG. 4. Intermediate layer 807 may cover an entirety of upper internal structure 806 and may be positioned under upper internal structure 806 (e.g., on top of inner mold 802). Substrate 808 fill a gap between inner mold 802 and intermediate layer 807. Substrate 808 may be similar to substrate 404 of FIG. 4 and may be inoculated with one or more selected fungal strains, such as the strains discussed above with respect to FIGS. 3-6B.

As appreciated by FIG. 8, hyphae 810 may grow from substrate 808 to outer mold 804, thereby growing around and/or through intermediate layer 807 and upper internal structure 806, similar to the hyphae growth described above with respect to FIGS. 3 and 4. When the growing hyphae contact the outer mold 804, the hyphae may form a skin, as described above with respect to FIG. 3.

In some examples, to prevent mycelium growth in undesired regions, one or more barriers may be formed from and/or coupled to outer mold 804. The one or more barriers may be a physical barrier that prevents and contains mycelium growth, such as a plastic barrier that extends outward. In other examples, the one or more barriers may be a chemical barrier. For example, a barrier may include antifungal compounds to prevent mycelium growth. The barrier(s) may facilitate formation of eyelets to accommodate laces, for example. In other examples, eyelets or other voids may be cut out of the final upper after it is formed.

Thus, once the fungal strain(s) inoculated on substrate 808 begins to grow, a plurality of branched hyphae (shown generally at 810) may extend outward from substrate 808, growing through and/or around intermediate layer 807 and upper internal structure 806. It is to be understood that the entirety of substrate 808 (at least where substrate 808 has been inoculated and includes nutrients and where no barriers are present) may include hyphae growing around and outward from it, but that only a portion of the hyphae is shown so that underlying structures are more visible. During hyphae growth, the conditions surrounding and/or within system 800 may be controlled to generate desired properties of the resultant mycelium. For example, system 800 may be placed in a chamber to control air exchange, limit light exposure, etc. The air in and/or surrounding system 800 may be controlled to have a specific O2 and/or CO2 content, temperature, and/or humidity, which may all affect the growth properties of the hyphae. The growing hyphae may be manipulated directly, such as by mechanical pressure, deformation, chemical growth promotors or inhibitors, and so forth.

Once the mycelium has grown to a desired thickness and/or density, the outer mold 804 may be removed and the upper internal structure/mycelium biocomposite material delaminated from the intermediate layer, leaving in place an upper. The upper may then be processed via a suitable process to ensure the resultant material is water resistant, shielded from mycelium degradation, and/or other desired properties. The upper may be further modified to include a lacing system, a tongue, modified regions (e.g., embossed, debossed, etched), etc., and then the upper may be incorporated into an article of footwear as described above with respect to FIGS. 3, 4, and 7.

While system 800 is described above as being configured for forming an upper for an article of footwear, a similar system may be used to generate other wearable articles. For example, a hat, gloves, shirt, pants, socks, etc., may be formed using a system that includes a 3D inner mold (which may be in the shape of the wearable article), an outer mold in the shape of the wearable article, an internal structure, and a substrate inoculated with a fungal strain. Upon mycelium growth from the fungal strain, one or more layers of mycelium may be grown over, under, and/or through the internal structure to form a biocomposite material having zonal properties, where the zonal properties include zones with the internal structure and the mycelium, and zones without the internal structure and only the mycelium, and/or where the zonal properties include the internal structure having zones/regions of different density, thickness, material properties, etc.

FIG. 9 is a flow chart illustrating a method 900 for forming an upper of an article of footwear from a biocomposite material grown around a 3D mold. For example, an upper of shoe 100 and/or shoe 202 may be formed according to method 900 using system 800, for example.

At 902, an upper internal structure is prepared. The upper internal structure may be similar to upper internal structure 806 described above, and may be generated by 3D printing, as indicated at 904. When the upper internal structure is 3D printed, the upper internal structure may be comprised of PLA or other biodegradable material that is capable of being 3D printed. In some examples, rather than use a biodegradable material, the upper internal structure may be 3D printed from acrylonitrile butadiene styrene (ABS) or other polymer. However, additionally or alternatively, the upper internal structure may be generated by knitting, braiding, weaving, or other techniques, as indicated at 906. For example, the upper internal structure may be comprised of a knit or woven fabric, such as cotton, wool, etc. Additionally, in some examples, the upper internal structure may include zones of different material properties, as indicated at 908. The different material properties may include different materials, different density of material, different factor of the material, different thickness of material, and so forth, as explained above with respect to upper internal structure 304 of FIG. 3.

At 910, the upper internal structure is positioned between an inner mold and an outer mold, such as inner mold 802 and outer mold 804 described above with respect to FIG. 8. At 912, a gap between the upper internal structure and inner mold is filled with a substrate that is inoculated with desired fungal strain(s). Further, an intermediate layer may be positioned in the gap, adjacent and/or directly contacting the upper internal structure, before the substrate is added to the gap. However, in some examples, the inoculated substrate may be placed on the inner mold, and then the intermediate layer, upper internal structure, and outer mold may be placed on the substrate.

At 914, the mycelium growth conditions may be manipulated to obtain a desired appearance, material properties, etc., of the resultant mycelium composite material. The mycelium growth conditions may be manipulated indirectly, such as through ambient conditions (e.g., O2 and/or CO2 content, humidity, supplied nutrients, light, temperature) and/or directly, such as through mechanical pressure, "combing" of the mycelium (e.g., adjusting the directionality of the branching hyphae), voids or antifungal material to inhibit growth in certain regions, and so forth.

At 916, once mycelium growth is complete, the inner mold and outer mold are removed and the mycelium-internal structure composite material is removed from the substrate. For example, the inclusion of the intermediate layer may allow for the substrate to be removed without causing damage to the upper.

At 918, the mycelium-based upper is processed into a final upper for incorporation into an article of footwear. The processing may include tanning the upper to remove residual water while preserving the mycelium structure and protecting the upper from degradation. The processing may include dying the upper to achieve one or more desired colors, adding a lacing system, and so forth. Method 900 then ends.

Thus, method 900 provides for growing an upper from mycelium using a mold structure comprised of a 3D inner mold and an outer mold in the shape of the final upper and an internal structure positioned between the molds. The mycelium may grow from substrate present between the inner mold and internal structure, thereby form an upper. Voids to accommodate laces and/or other structures may be formed via the mold structure (e.g., by the inclusion of barriers, varying material properties in the internal structure, and so forth) or the voids and/or additional structures may be cut or added after the mycelium is grown (e.g., during or after processing). Further, differing material properties in the upper may be provided by including an internal structure in the upper, through which the mycelium may grow. The internal structure may include desired material densities, thickness, flexibility, and strength, which may be mimicked in the growing mycelium and final formed upper.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A biocomposite material, comprising:
   a biopolymer material; and
   an internal structure imparting zonal properties to the biocomposite material, the internal structure comprising a first region having a first density, and a second region having a second density, wherein the first density is greater than the second density, where the biopolymer material includes mycelium grown from a fungal strain;
   wherein the internal structure is permeable to mycelium growth; and
   wherein the mycelium is grown through and around the internal structure.

2. The biocomposite material of claim 1, wherein the internal structure has regions of differing thickness and/or material properties.

3. The biocomposite material of claim 1, wherein the internal structure is comprised of polylactic acid, a woven material, a braided material, and/or a knit material.

4. The biocomposite material of claim 1, wherein the internal structure is comprised of two or more pieces.

5. The biocomposite material of claim 1, wherein the biocomposite material having zonal properties includes the biocomposite material having a first zone and a second zone, the first zone comprised of only the biopolymer material and the second zone comprised of both the biopolymer material and the internal structure.

6. The biocomposite material of claim 1, wherein the biocomposite material having zonal properties includes the biocomposite material having a first zone and a second zone, the first zone comprised of the biopolymer material and a first region of the internal structure and the second zone comprised of the biopolymer material and a second region of the internal structure, where the first region and second region differ in thickness, density, and/or material properties.

7. The biocomposite material of claim 1, wherein the fungal strain is *Ganoderma lucidum*.

8. A biocomposite material, comprising:
   mycelium; and
   an internal structure comprised of polylactic acid, a woven material, a braided material, and/or a knit material and comprising regions of differing thickness, density, and/or material properties to thereby impart zonal properties to the biocomposite material, wherein the mycelium is grown from a substrate, through an intermediate layer positioned between the substrate and the internal structure, and through the internal structure.

9. The biocomposite material of claim 8, wherein the mycelium is from a *Ganoderma lucidum* fungal strain.

10. The biocomposite material of claim 8, wherein the internal structure is comprised of two or more pieces.

11. The biocomposite material of claim 8, wherein the biocomposite material includes a first region having a density and/or material property that changes along a first axis and a second region having a uniform density and/or material property along a second axis, parallel to the first axis.

12. An article of footwear comprising:
   an upper internal structure having a lacing zone, a toe zone, and side zones, wherein the upper internal structure is permeable to mycelium growth; and
   mycelium grown from a substrate, the mycelium comprising a plurality of branching-type hyphae grown through and around the upper internal structure such that the upper internal structure is incorporated into an intermediate region of a final upper such that one or more layers of mycelium are present below the upper internal structure and one or more layers or mycelium are present above the upper internal structure,
   wherein the upper internal structure influences a density of the mycelium, a hyphae growth direction, and a hyphae branching directionality.

13. The biocomposite material of claim 8, wherein the intermediate layer facilitates uniform separation of the mycelium from the substrate.

14. The biocomposite material of claim 8, wherein the intermediate layer comprises areas permeable to mycelium growth and areas impermeable to mycelium growth.

15. The biocomposite material of claim 14, wherein the areas impermeable to mycelium growth correspond to openings in the biocomposite material.

* * * * *